United States Patent
Allphin et al.

(10) Patent No.: US 10,195,151 B2
(45) Date of Patent: Feb. 5, 2019

(54) FORMULATIONS OF (R)-2-AMINO-3-PHENYLPROPYL CARBAMATE

(71) Applicant: Jazz Pharmaceuticals International III Limited, Hamilton (BM)

(72) Inventors: Clark Patrick Allphin, Seattle, WA (US); Edwin Gerard Walsh, Dublin (IE)

(73) Assignee: Jazz Pharmaceuticals International III Limited, Hamilton (BM)

( * ) Notice: Subject to any disclaimer, the term of this patent is extended or adjusted under 35 U.S.C. 154(b) by 0 days.

(21) Appl. No.: 15/695,913

(22) Filed: Sep. 5, 2017

(65) Prior Publication Data

US 2018/0064652 A1 Mar. 8, 2018

Related U.S. Application Data

(60) Provisional application No. 62/383,818, filed on Sep. 6, 2016.

(51) Int. Cl.
A61K 9/20 (2006.01)
A61K 31/27 (2006.01)
A61K 31/165 (2006.01)

(52) U.S. Cl.
CPC .......... *A61K 9/2054* (2013.01); *A61K 9/2068* (2013.01); *A61K 31/165* (2013.01); *A61K 31/27* (2013.01)

(58) Field of Classification Search
CPC .. A61K 9/2054; A61K 9/2068; A61K 31/165; A61K 31/27
See application file for complete search history.

(56) References Cited

U.S. PATENT DOCUMENTS

| | | |
|---|---|---|
| 5,705,640 A | 1/1998 | Choi et al. |
| 5,756,817 A | 5/1998 | Choi et al. |
| 5,955,499 A | 9/1999 | Choi et al. |
| 6,140,532 A | 10/2000 | Choi et al. |
| 6,680,299 B2 | 1/2004 | Or et al. |
| 6,680,322 B2 | 1/2004 | Castelhano et al. |
| 6,680,324 B2 | 1/2004 | Castelhano et al. |
| 8,232,315 B2 | 7/2012 | Lee et al. |
| 8,440,715 B2 | 5/2013 | Ahnaou et al. |
| 8,552,060 B2 | 10/2013 | Palumbo et al. |
| 8,623,913 B2 | 1/2014 | Melnick et al. |
| 8,729,120 B2 | 5/2014 | Sporn |
| 8,741,950 B2 | 6/2014 | Khayrallah et al. |
| 8,778,398 B2 * | 7/2014 | Rourke ................ A61K 31/191 424/479 |
| 8,895,609 B2 | 11/2014 | Lee et al. |
| 8,927,602 B2 | 1/2015 | Lee et al. |
| 8,952,062 B2 | 2/2015 | Cook et al. |

(Continued)

OTHER PUBLICATIONS

Aulton, "Dissolution and solubility", Aug. 2, 2015, retrieved from https://clinicalgate.com/dissolution-and-solubility on May 13, 2018. Year: 2015).*

(Continued)

*Primary Examiner* — Jianfeng Song (74) *Attorney, Agent, or Firm* — Myers Bigel, P.A.

(57) ABSTRACT

The present invention relates to immediate release formulations of (R)-2-amino-3-phenylpropyl carbamate and methods of using the same to treat disorders.

21 Claims, 4 Drawing Sheets

(56) References Cited

U.S. PATENT DOCUMENTS

| | | |
|---|---|---|
| 9,050,302 B2 | 6/2015 | Eller |
| 9,226,910 B2 | 1/2016 | Khayrallah et al. |
| 9,359,290 B2 | 6/2016 | Khayrallah et al. |
| 2011/0111027 A1 | 5/2011 | Rourke et al. |
| 2012/0004300 A1 | 1/2012 | Lee et al. |
| 2014/0275244 A1* | 9/2014 | Khayrallah ........... C07C 271/00 514/489 |
| 2014/0350098 A1 | 11/2014 | Ahnaou et al. |
| 2015/0018414 A1 | 1/2015 | Khayrallah et al. |
| 2015/0246874 A1 | 9/2015 | Kang et al. |
| 2016/0081970 A1 | 3/2016 | Khayrallah et al. |

OTHER PUBLICATIONS

Notification of Transmittal of the International Search Report and the Written Opinion of the International Searching Authority, or the Declaration corresponding to International Application No. PCT/US2017/050221 dated Nov. 13, 2017.

* cited by examiner

| SET | TIME (MINUTES) | | | | | | | | STD | TOTAL | F2 |
|---|---|---|---|---|---|---|---|---|---|---|---|
| | 0 | 2 | 5 | 10 | 15 | 20 | 25 | 30 | | | |
| 4 | 0% | 20% | 45% | 80% | 98% | 97% | 100% | 103% | 163.5 | 182.7 | 74.5 |
| 6 | 0% | 18% | 50% | 80% | 94% | 99% | | | 151.4 | 163.3 | * |

*FIG. 1*

| SET | TIME (MINUTES) | | | | | | | | STD | TOTAL | F2 |
|---|---|---|---|---|---|---|---|---|---|---|---|
| | 0 | 2 | 5 | 10 | 15 | 20 | 25 | 30 | | | |
| 1 | 0% | 20% | 57% | 85% | 97% | 99% | 98% | 100% | 148.6 | 164.4 | 75.9 |
| 2 | 0% | 16% | 57% | 89% | 96% | 100% | 100% | 100% | 150.8 | 166.4 | * |
| 3 | 0% | 11% | 57% | 92% | 100% | 101% | | | 154.4 | 172.6 | 71.5 |
| 4 | 0% | 20% | 45% | 80% | 98% | 97% | 100% | 103% | 163.5 | 182.7 | 52.8 |

FIG. 2

| SET | TIME (MINUTES) | | | | | | | | STD | TOTAL | F2 |
|---|---|---|---|---|---|---|---|---|---|---|---|
| | 0 | 2 | 5 | 10 | 15 | 20 | 25 | 30 | | | |
| 5 | 0% | 26% | 61% | 93% | 100% | | | | 149.2 | 78.77 | 48.5 |
| 6 | 0% | 18% | 50% | 80% | 94% | 99% | | | 151.4 | 163.3 | * |
| 7 | 0% | 13% | 37% | 66% | 86% | 96% | 99% | | 153.7 | 345.7 | 48.3 |

FORMULATIONS OF (R)-2-AMINO-3-PHENYLPROPYL CARBAMATE

STATEMENT OF PRIORITY

The present invention claims the benefit, under 35 U.S.C. § 119(e), of U.S. Provisional Application No. 62/383,818, filed Sep. 6, 2016, the entire contents of which are incorporated by reference herein.

FIELD OF THE INVENTION

The present invention relates to immediate release formulations of (R)-2-amino-3-phenylpropyl carbamate (APC) and methods of using the same to treat disorders.

BACKGROUND OF THE INVENTION

APC is a phenylalanine analog that has been demonstrated to be useful in the treatment of a variety of disorders, including excessive daytime sleepiness, cataplexy, narcolepsy, fatigue, depression, bipolar disorder, fibromyalgia, and others. See, for example, U.S. Pat. Nos. 8,232,315; 8,440,715; 8,552,060; 8,623,913; 8,729,120; 8,741,950; 8,895,609; 8,927,602; 9,226,910; and 9,359,290; and U.S. Publication Nos. 2012/0004300 and 2015/0018414. Methods for producing APC (which also has other names) and related compounds can be found in U.S. Pat. Nos. 5,955,499; 5,705,640; 6,140,532 and 5,756,817. All of the above patents and applications are hereby incorporated by reference in their entireties for all purposes.

The present invention overcomes shortcomings in the art by providing immediate release formulations of APC suitable for treatment of disorders responsive to APC.

SUMMARY OF THE INVENTION

The present invention relates to the development of immediate release formulations of APC. The invention additionally relates to the use of the formulations for the treatment of disorders responsive to APC.

Accordingly, one aspect of the invention relates to an immediate release compressed tablet for oral delivery of APC, the tablet comprising:
APC or a pharmaceutically acceptable salt thereof in an amount of about 90-98% by weight of the tablet;
at least one binder in an amount of about 1-5% by weight of the tablet; and
at least one lubricant in an amount of about 0.1-2% by weight of the tablet;
wherein the tablet releases at least 85% of the APC or a pharmaceutically acceptable salt thereof contained therein within a period of less than 15 minutes after administration of the tablet to a subject.

The invention further relates to an immediate release oral dosage form of APC, the oral dosage form comprising:
APC or a pharmaceutically acceptable salt thereof in an amount of about 90-98% by weight of the oral dosage form;
at least one binder in an amount of about 1-5% by weight of the oral dosage form; and
at least one lubricant in an amount of about 0.1-2% by weight of the oral dosage form;
wherein the oral dosage form releases at least 85% of the APC or a pharmaceutically acceptable salt thereof contained therein within a period of less than 15 minutes after administration of the oral dosage form to a subject.

The invention also relates to an immediate release compressed tablet for oral delivery of APC, the tablet comprising APC or a pharmaceutically acceptable salt thereof in an amount of about 90-98% by weight of the tablet; wherein the tablet exhibits substantially identical dissolution rates of the APC or a pharmaceutically acceptable salt thereof at pH 1.2, pH 4.5, and pH 6.8.

The invention further relates to a method of treating a disorder amenable to treatment with APC, e.g., narcolepsy, cataplexy, excessive daytime sleepiness, drug addiction, sexual dysfunction, fatigue, fibromyalgia, attention deficit/hyperactivity disorder, restless legs syndrome, depression, bipolar disorder, or obesity in a subject in need thereof, or promoting smoking cessation in a subject in need thereof, comprising administering to the subject the compressed tablet of the invention.

The present invention is explained in greater detail in the drawings herein and the specification set forth below.

DETAILED DESCRIPTION OF THE INVENTION

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety for all purposes.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

A "disorder amenable to treatment with APC" refers to any disorder in which administration of APC to a subject results in the treatment of one or more symptoms of the disorder in the subject. Examples of such disorders include, without limitation, narcolepsy, cataplexy, excessive daytime sleepiness, drug addiction, sexual dysfunction, fatigue, fibromyalgia, attention deficit/hyperactivity disorder, restless legs syndrome, depression, bipolar disorder, or obesity.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; 21st ed. 2005).

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The present invention provides formulations and dosage forms for the immediate release of APC or a pharmaceutically acceptable salt thereof. Formulations described herein are suited to the immediate release of high dose drugs that are highly water soluble. In particular embodiments, the immediate release formulations are provided as a unit dosage form, and in certain embodiments, the immediate release formulation is provided as an immediate release tablet.

In certain embodiments, the immediate release APC compositions described herein comprise a therapeutically effective amount of APC or an alternative salt thereof. The structure of the free base of APC is given below as formula I.

(1)

Administration of APC in solid form presents several challenges. Patients treated with APC may have difficulty taking solid medications by mouth because they have disease states that make handling and swallowing difficult. Accordingly, it is desirable to keep the size of the tablet as small as possible while incorporating the largest amount of active ingredient and meeting the desired dissolution profile. In addition, it is desirable to have a formulation that dissolves quickly without high levels of excipients to speed dissolution.

Accordingly, one aspect of the invention relates to an immediate release compressed tablet for oral delivery of APC, the tablet comprising:

APC or a pharmaceutically acceptable salt thereof in an amount of about 90-98% by weight of the tablet;

at least one binder in an amount of about 1-5% by weight of the tablet; and at least one lubricant in an amount of about 0.1-2% by weight of the tablet;

wherein the tablet releases at least 85% of the APC or a pharmaceutically acceptable salt thereof contained therein within a period of less than 15 minutes after administration of the tablet to a subject.

In one embodiment, the tablet comprises:

APC or a pharmaceutically acceptable salt thereof in an amount of about 91-95% by weight of the tablet;

at least one binder in an amount of about 2-3% by weight of the tablet;

at least one lubricant in an amount of about 0.1-1% by weight of the tablet; and optionally, a cosmetic film coat in an amount of about 3-4% by weight of the tablet;
wherein the tablet releases at least 85% of the APC or a pharmaceutically acceptable salt thereof contained therein within a period of less than 15 minutes after administration of the tablet to a subject.

In one embodiment, the tablet comprises:
APC or a pharmaceutically acceptable salt thereof in an amount of about 93.22% by weight of the tablet;
at least one binder (e.g., hydroxypropylcellulose) in an amount of about 2.87% by weight of the tablet;
at least one lubricant (e.g., magnesium stearate) in an amount of about 0.52% by weight of the tablet; and
optionally, a cosmetic film coat (e.g., Opadry® 11 yellow) in an amount of about 3-4% by weight of the tablet;
wherein the tablet releases at least 85% of the APC or a pharmaceutically acceptable salt thereof contained therein within a period of less than 15 minutes after administration of the tablet to a subject.

The invention further relates to an immediate release oral dosage form of APC, the oral dosage form comprising:
APC or a pharmaceutically acceptable salt thereof in an amount of about 90-98% by weight of the oral dosage form;
at least one binder in an amount of about 1-5% by weight of the oral dosage form; and
at least one lubricant in an amount of about 0.1-2% by weight of the oral dosage form;
wherein the oral dosage form releases at least 85% of the APC or a pharmaceutically acceptable salt thereof contained therein within a period of less than 15 minutes after administration of the oral dosage form to a subject.

The formulations and unit dosage forms provided herein can be utilized to achieve immediate release of APC, as well as pharmaceutically acceptable salts, hydrates, isomers, including tautomers, solvates and complexes of APC.

Suitable salts of APC include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts. In certain embodiments, the salt is the hydrochloride salt.

Compounds of the formulae herein include those having quaternization of any basic nitrogen-containing group therein.

The discussion herein is, for simplicity, provided without reference to stereoisomerism. Those skilled in the art will appreciate that the compounds of the invention can contain one or more asymmetric centers and thus occur as racemates and racemic mixtures and single optical isomers. All such isomeric forms of these compounds are expressly included in the present invention.

Unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

The discussion herein is also provided without reference to polymorphs, hydrates, clathrates, solvates, inclusion compounds, isomers, or other forms of the compound. All such forms of these compounds are expressly included in the present invention.

Further, the compounds of the invention include prodrugs of the compounds that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; a N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. No. 6,680,324 and U.S. Pat. No. 6,680,322.

The term "pharmaceutically acceptable prodrug" (and like terms) as used herein refers to those prodrugs of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

In some embodiments, the tablet releases at least 85%, 86%, 87%, 88%, 89%, 90%, 91%, 92%, 93%, 94%, 95%, 96%, 97%, 98%, or 99% of APC or a pharmaceutically acceptable salt thereof contained therein within a period of less than 15 minutes after administration of the tablet to a subject, e.g., less than 15, 14, 13, 12, 11, 10, 9, 8, 7, 6, or 5 minutes. In some embodiments, the tablet releases at least 95%, 96%, 97%, 98%, or 99% of APC or a pharmaceutically acceptable salt thereof contained therein within a period of less than 30 minutes after administration of the tablet to a subject.

In certain embodiments, the tablet does not comprise a disintegrant. The term "disintegrant," as used herein, refers to an agent added to a tablet to promote the breakup of the tablet in an aqueous environment. The tablets of the present invention are advantageous in that they dissolve rather than disintegrate. In the present invention the presence of disintegrant in the formulation may actually slow down release of APC.

In certain embodiments, APC or a pharmaceutically acceptable salt thereof is present in an amount of about 90%, 90.5%, 91%, 91.5%, 92%, 92.5%, 93%, 93.5%, 94%, 94.5%, 95%, 95.5%, 96%, 96.5%, 97%, 97.5%, or 98% by weight of the tablet or any value or range therein. In certain embodiments, APC or a pharmaceutically acceptable salt thereof is present in an amount of about 90% to about 98%, about 92% to about 98%, about 94% to about 98%, about 96% to about 98%, about 90% to about 92%, about 90% to about 94%, about 90% to about 96%, about 92% to about 94%, about 92% to about 96%, or about 94% to about 96%.

In certain embodiments, the at least one binder is present in an amount of about 1%, 1.5%, 2%, 2.5%, 3%, 3.5%, 4%, 4.5%, or 5% by weight of the tablet or any value or range therein. In certain embodiments, the at least one binder is present in an amount of about 1% to about 5%, about 2% to about 5%, about 3% to about 5%, about 4% to about 5%, about 1% to about 2%, about 1% to about 3%, about 1% to about 4%, about 2% to about 3%, about 2% to about 4%, or about 3% to about 4%. The tablet may comprise at least one binder, e.g., 1, 2, 3, 4, 5, or more binders.

In certain embodiments, the at least one binder is selected from at least one of hydroxypropyl cellulose, ethylcellulose, hydroxypropyl methylcellulose, polyvinyl alcohol, hydroxyethyl cellulose, povidone, copovidone, pregelatinized starch, dextrin, gelatin, maltodextrin, starch, zein, acacia, alginic acid, carbomers (cross-linked polyacrylates), polymethacrylates, sodium carboxymethylcellulose, guar gum, hydrogenated vegetable oil (type 1), methylcellulose, magnesium aluminum silicate, and sodium alginate or any combination thereof. In some embodiments, the at least one binder is hydroxypropyl cellulose.

In certain embodiments, the at least one lubricant is present in an amount of about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% by weight of the tablet or any value or range therein. In certain embodiments, the at least one lubricant is present in an amount of about 0.1% to about 2.0%, about 0.5% to about 2.0%, about 1.0% to about 2.0%, about 1.5% to about 2.0%, about 0.1% to about 0.5%, about 0.1% to about 1.0%, about 0.1% to about 1.5%, about 0.5% to about 1.0%, about 0.5% to about 1.5%, or about 1.0% to about 1.5%. The tablet may comprise at least one lubricant, e.g., 1, 2, 3, 4, 5, or more lubricants. Where the immediate release formulation is provided as a tableted dosage form, still lower lubricant levels may be achieved with use of a "puffer" system during tableting. Such systems are known in the art, commercially available and apply lubricant directly to the punch and die surfaces rather than throughout the formulation.

In certain embodiments, the at least one lubricant is selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate or any combination thereof. In some embodiments, the at least one lubricant is magnesium stearate. In other embodiments, magnesium stearate may be used in combination with one or more other lubricants or a surfactant, such as sodium lauryl sulfate. In particular, if needed to overcome potential hydrophobic properties of magnesium stearate, sodium lauryl sulfate may also be included when using magnesium stearate (Remington: the Science and Practice of Pharmacy, 20$^{th}$ edition, Gennaro, Ed., Lippincott Williams & Wilkins (2000)).

In some embodiments, the at least one binder is hydroxypropyl cellulose. In some embodiments, the at least one lubricant is magnesium stearate. In some embodiments, the at least one binder is hydroxypropyl cellulose and the at least one lubricant is magnesium stearate.

In certain embodiments, the tablet is coated. The coating may be, without limitation, a color overcoat.

In some embodiments, the APC or a pharmaceutically acceptable salt thereof is APC hydrochloride.

The tablet may be any shape that is suitable for immediate release and allows the release of at least 85% of the APC or a pharmaceutically acceptable salt thereof contained therein within a period of less than 15 minutes after administration of the tablet to a subject. In some embodiments, the tablet maximizes surface area to volume ratio to promote rapid dissolution. In some embodiments, the tablet is oblong in shape.

The tablet may contain any amount of APC or a pharmaceutically acceptable salt thereof suitable for administration as a unit dosage form. In some embodiments, the tablet contains about 1 mg to about 1000 mg of the drug or any range or value therein, e.g., about 10 mg to about 500 mg, e.g., about 37.5 mg, about 75 mg, about 150 mg, or about 300 mg.

APC or a pharmaceutically acceptable salt thereof may be obtained or synthesized by methods known in the art and as described herein. Details of reaction schemes for synthesizing APC have been described in U.S. Pat. Nos. 5,705,640; 5,756,817; 5,955,499; and 6,140,532, all incorporated herein by reference in their entirety.

"Immediate release" as used herein, refers to a composition that releases APC or a pharmaceutically acceptable salt, hydrate, isomer, tautomer, solvate or complex thereof substantially completely into the gastrointestinal tract of the user within a period of less than about 15 minutes, usually between about 1 minute and about 15 minutes from ingestion. Such a delivery rate allows the drug to be absorbed by the gastrointestinal tract in a manner that is bioequivalent to an oral solution. Such rapid absorption will typically occur for an immediate release unit dosage form, such as a tablet, caplet or capsule, if the drug included in such dosage form dissolves in the upper portion the gastrointestinal tract.

Release rates can be measured using standard dissolution test methods. For example, the standard conditions may be those described in FDA guidance (e.g., 50 rpm, 37° C., USP 2 paddles, pH 1.2 and pH 6.8 media, 900 ml, 1 test article per vessel).

"Dissolution rate," as used herein, refers to the quantity of drug released in vitro from a dosage form per unit time into a release medium.

"Bioavailability," as used herein, refers to the estimated area under the curve, or AUC of the active drug in systemic circulation after oral administration with a dosage form as disclosed herein when compared with the AUC of the active drug in systemic circulation after intravenous administration of the active drug. The AUC is affected by the extent to which the drug is absorbed in the GI tract.

Products are considered to be "bioequivalent" if the relative mean $C_{max}$, $AUC_{(0-t)}$ and $AUC_{(0-\infty)}$ of the test product to reference product is within 80% to 125%.

The term "$AUC_{(0-t)}$" means the area under the plasma concentration curve from time 0 to time t.

The term "$AUC_{(0-\infty)}$" or "$AUC_{0-inf}$" means the area under the plasma concentration time curve from time 0 to infinity.

"$C_{max}$" refers to the maximum plasma concentration of APC.

"$T_{max}$" refers to the time to maximum plasma concentration for a given drug.

"$t_{1/2}$" refers to the time to reduce the plasma concentration by 50% during the terminal elimination phase of the drug.

Immediate release formulations suitable for oral administration may comprise unit dosage forms, such as tablets, caplets or filled capsules, which can deliver a therapeutically effective dose of APC upon ingestion thereof by the patient of one or more of said dosage forms, each of which can provide a dosage of, for example, about 1 to about 1000 mg of APC. Additionally, the immediate release dosage forms can be shaped or scored to facilitate dose adjustment through tablet splitting.

The formulation and structure of an immediate release dosage form as disclosed herein can be adjusted to provide immediate release performance that suits a particular dosing need. In particular, the formulation and structure of the dosage forms as described herein can be adjusted to provide any combination of the immediate release performance characteristics described herein. In particular embodiments, for example, an immediate release dosage form as disclosed herein provides rapid onset of action, releasing more than about 85%, such as, for example, more than about 90% or 95%, of the drug contained therein within a period of time selected from less than 15 minutes, less than 12 minutes, less than 10 minutes, and less than 5 minutes after administration.

Moreover, the rate of drug release from an immediate release dosage form as disclosed herein may be adjusted as needed to facilitate a desired dosing regimen or achieve targeted dosing. In one embodiment, the immediate release dosage form may be formulated to deliver as much as 1,000 mg of APC. In particular embodiments, the total amount of drug contained within an immediate release dosage form according to the present description may be between about 10 mg and about 500 mg. For example, in certain such embodiments, the total amount of drug may be selected from about 10, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg or any range or value therein. In certain such embodiments, the total amount of drug may be about 10 mg to about 1000 mg, about 10 mg to about 500 mg, about 10 mg to about 300 mg, about 30 mg to about 1000 mg, about 30 mg to about 500 mg, about 30 mg to about 300 mg, about 100 mg to about 1000 mg, about 10 mg to about 500 mg, about 100 mg to about 300 mg, about 150 mg to about 1000 mg, about 150 mg to about 500 mg, or about 150 mg to about 300 mg.

The immediate release formulations provided herein generally include APC and some level of lubricant to facilitate processing of the formulations into a unit dosage form. In some embodiments, therefore, the formulations described herein include a combination of APC and lubricant, as described herein, and in certain such embodiments, the immediate release formulations are substantially free of other excipients or adjuvants. In other embodiments, the immediate release formulations described herein include a combination of APC, lubricant, and binder, as described herein, and in certain such embodiments, the immediate release formulations are substantially free of other excipients or adjuvants. Though the immediate release formulations described herein may be formulated using a combination of drug and one or more of a lubricant and binder, in certain embodiments, the compositions described herein may include one or more additional excipients selected from, for example, fillers, compression aids, diluents, disintegrants, colorants, flavorants, buffering agents, coatings, glidants, or other suitable excipients.

The immediate release formulations described herein may be manufactured using standard techniques, such as wet granulation, roller compaction, fluid bed granulation, and dry powder blending. Suitable methods for the manufacture of the immediate release formulations and unit dosage forms described herein are provided, for example, in Remington, 20$^{th}$ edition, Chapter 45 (Oral Solid Dosage Forms). It has been found that, even without the aid of binders or non-lubricating excipients, such as compression aids, wet granulation techniques can afford flowable granules with compression characteristics suitable for forming unit dosage forms as described herein. Therefore, in certain embodiments, where a drug content greater than about 85%, 90% or 95% by weight is desired for the immediate release formulation, wet granulation techniques may be used to prepare immediate release formulations as described herein. In such embodiments, as illustrated in the Examples provided herein, conventional organic or aqueous solvents may be used in the wet granulation process. Suitable wet granulation processes can be performed as fluidized bed, high shear, or low shear (wet massing) granulation techniques, as are known in the art.

In addition to one or more of APC, lubricant, and binder, where desired, the immediate release formulations described herein may also include fillers or compression aids selected from at least one of lactose, calcium carbonate, calcium sulfate, compressible sugars, dextrates, dextrin, dextrose, kaolin, magnesium carbonate, magnesium oxide, maltodextrin, mannitol, microcrystalline cellulose, powdered cellulose, and sucrose. Where a filler or compression aid is used, in certain embodiments, it may be included in the immediate release formulation in an amount ranging from about 1%-15% by weight.

Immediate release formulations as described herein may be processed into unit dosage forms suitable for oral administration, such as for example, filled capsules, compressed tablets or caplets, or other dosage form suitable for oral administration using conventional techniques. Immediate release dosage forms prepared as described may be adapted for oral administration, so as to attain and maintain a therapeutic level of APC over a preselected interval. In certain embodiments, an immediate release dosage form as described herein may comprise a solid oral dosage form of any desired shape and size including round, oval, oblong, cylindrical, or polygonal. In one such embodiment, the surfaces of the immediate release dosage form may be flat, round, concave, or convex. In some embodiments, the shape may be selected to maximize surface area, e.g., to increase the rate of dissolution of the dosage form.

In particular, when the immediate release formulations are prepared as a tablet, the immediate release tablets contain a relatively large percentage and absolute amount of APC and so are expected to improve patient compliance and convenience, by replacing the need to ingest large amounts of liquids or liquid/solid suspensions. One or more immediate release tablets as described herein can be administered, by oral ingestion, e.g., closely spaced, in order to provide a therapeutically effective dose of APC to the subject in a relatively short period of time. For example, dissolution of a 10 mg-1000 mg tablet prepared according to the present description can provide about 80-100% of the APC to the subject in about 10-15 minutes.

Where desired or necessary, the outer surface of an immediate release dosage form as disclosed herein may be coated with a moisture barrier layer using materials and methods known in the art. For example, where the APC delivered by the unit dosage form is highly hygroscopic, providing a moisture barrier layer over the immediate release dosage form as disclosed herein may be desirable. For example, protection of an immediate release dosage form as disclosed herein from water during storage may be provided or enhanced by coating the tablet with a coating of a substantially water soluble or insoluble polymer. Useful water-insoluble or water-resistant coating polymers include ethyl cellulose and polyvinyl acetates. Further water-insoluble or water resistant coating polymers include polyacrylates, polymethacrylates or the like. Suitable water-soluble polymers include polyvinyl alcohol and HPMC. Further suitable water-soluble polymers include PVP, HPC, HPEC, PEG, HEC and the like.

Where desired or necessary, the outer surface of an immediate release dosage form as disclosed herein may be coated with a color overcoat or other aesthetic or functional layer using materials and methods known in the art.

APC is a highly water soluble compound but in a pH dependent manner. The solubility decreases about 20-fold around pH 7 as shown in Table 1. The skilled artisan might expect such a large drop in solubility would result in a change in dissolution as solubility drives the gradient which typically determines dissolution. Surprisingly, APC exhibits a consistent dissolution rate at different pHs above and below the solubility turning point. Further, the lack of a media pH effect has been consistently observed across doses ranging from 37.5 mg to 300 mg.

Thus, one aspect of the invention relates to an immediate release compressed tablet for oral delivery of APC, the tablet comprising APC or a pharmaceutically acceptable salt thereof in an amount of about 90-98% by weight of the tablet; wherein the tablet exhibits substantially identical dissolution rates of the APC or a pharmaceutically acceptable salt thereof at an acidic pH and a neutral pH, e.g., about pH 1.2, pH 4.5, and about pH 6.8. As used herein, the term "substantially identical dissolution rates" is defined as a ratio of the time for a percentage of APC to be released from a dosage form in one condition to the time for the same percentage of APC to be released from a dosage form in another condition in the range of about 1.3 to about 0.7.

In some embodiments, the tablet releases at least 85%, e.g., at least 85%, 86%, 87%, 88%, 89%, 90%, 91%, 92%, 93%, 94%, 95%, 96%, 97%, 98%, or 99%, of the APC or a pharmaceutically acceptable salt thereof contained therein within a period of less than 15 minutes after administration of the tablet to a subject.

In certain embodiments, the tablet comprises, consists essentially of, or consists of the components described above and has one or more of the characteristics described above.

Methods are disclosed herein to treat conditions amenable to treatment by APC, by administering an effective amount of one or more dosage forms as described herein. For example, the present dosage forms can be administered to treat a subject in need of treatment for narcolepsy, cataplexy, excessive daytime sleepiness, drug addiction, sexual dysfunction, fatigue, fibromyalgia, attention deficit/hyperactivity disorder, restless legs syndrome, depression, bipolar disorder, or obesity, or to promoting smoking cessation in a subject in need thereof. See, e.g., U.S. Pat. Nos. 8,232,315; 8,440,715; 8,552,060; 8,623,913; 8,729,120; 8,741,950; 8,895,609; 8,927,602; 9,226,910; and 9,359,290; and U.S. Publication Nos. 2012/0004300 and 2015/0018414; each of which is incorporated by reference in its entirety with respect to the disorder to be treated.

The dosage forms disclosed herein can also be provided as a kit comprising, separately packaged, a container comprising a plurality of immediate release tablets, which tablets can be individually packaged, as in foil envelopes or in a blister pack. The tablets can be packaged in many conformations with or without desiccants or other materials to prevent ingress of water. Instruction materials or means, such as printed labeling, can also be included for their administration, e.g., sequentially over a preselected time period and/or at preselected intervals, to yield the desired levels of APC in vivo for preselected periods of time, to treat a preselected condition.

A daily dose of about 1 to about 2000 mg of APC or a pharmaceutically acceptable salt thereof may be administered to accomplish the therapeutic results disclosed herein. For example, a daily dosage of about 10-1000 mg, e.g., about 20-500 mg, in single or divided doses, is administered. In some embodiments, the daily dose may be about 0.01 to about 150 mg/kg body weight, e.g., about 0.2 to about 18 mg/kg body weight.

In one embodiment of the invention, APC is administered to the subject as needed to treat a disorder. The compound can be administered continuously or intermittently. In one embodiment, the compound is administered to the subject more than once a day, e.g., 2, 3, or 4 times per day, or once every 1, 2, 3, 4, 5, 6, or 7 days. In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules, e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject. In another embodiment the compound can be administered to build up to a certain level, then maintained at a constant level and then a tailing dosage.

In one aspect of the invention, APC is delivered to a subject concurrently with an additional therapeutic agent. The additional therapeutic agent can be delivered in the same composition as the compound or in a separate composition. The additional therapeutic agent can be delivered to the subject on a different schedule or by a different route as compared to the compound. The additional therapeutic agent can be any agent that provides a benefit to the subject. Further agents include, without limitation, stimulants, antipsychotics, anti-depressants, agents for neurological disorders, and chemotherapeutic agents. One therapeutic agent that can be administered during the same period is Xyrem®, sold commercially by Jazz Pharmaceuticals, which is used to treat narcolepsy and cataplexy. See U.S. Pat. Nos. 8,952,062 and 9,050,302.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has a disorder amenable to treatment with APC. In other embodiments, the subject used in the methods of the invention is an animal model of a disorder amenable to treatment with APC.

The subject can be a subject "in need of" the methods of the present invention, e.g., in need of the therapeutic effects of the inventive methods. For example, the subject can be a subject that is experiencing a disorder amenable to treatment with APC, is suspected of having a disorder amenable to treatment with APC, and/or is anticipated to experience a disorder amenable to treatment with APC, and the methods and compositions of the invention are used for therapeutic and/or prophylactic treatment.

The present invention is explained in greater detail in the following non-limiting Examples.

Example 1

Immediate Release Formulation of (R)-2-amino-3-phenylpropyl carbamate hydrochloride Immediate release tablet formulations of APC were developed with the goal of achieving 85% dissolution in under 15 minutes. Dosage strengths of 75 mg, 150 mg, and 300 mg were targeted. The amount of APC per tablet was maximized to increase the release rate. A formulation of APC with binder and lubricant was found to maximize dissolution.

Tablets were prepared by first dry-blending screened hydroxypropylcellulose (HPC ExF, Ashland, 1.00 g)) and APC (unmilled, 19.00 g) and then wet granulating them in a bullet-type blender while adding 4 g water in 0.5 g increments. Sufficient granules were formed at 3 g, and at 4 g it was slightly over-wetted. The granules were wet sieved, dried partially to remove 0.7 g of moisture, and wet sieved again prior to drying at 60° C. for about 1 hour. Magnesium stearate (0.75% of formulation) was added with blending 24 turns in a plastic container.

The active granulation was compressed with 13/32" standard round tooling, 380 mg, 1 ton force applied by a Carver press to produce the 300 mg strength. The remaining tablets were compressed using 1 ton force and various size tooling.

Tablets were coated with a color overcoat (Aquarius Cool Vanilla BI-1800, Ashland/Aqualon; hydroxypropylmethylcellulose, titanium dioxide, triacetin, polysorbate) using a Caleva air-suspension coater to 2-4% by weight.

Dissolution testing was carried per FDA guidance under standard conditions (50 rpm, 37° C., USP 2 paddles, pH 1.2 and pH 6.8 media, 900 ml, 1 test article per vessel, sinkers for capsules). Samples were taken at 0, 2, 5, 10, 15, 20, 25, and 30 minutes with a tolerance of 2 seconds. After 30 minutes, the stirring speed was increase to 150 rpm for at least 1 minute or until all material had visibly dissolved or dispersed. The speed was then returned to 50 rpm and a sample indicating the total dissolved dose was taken. Samples were diluted 1.00 ml in 8.00 ml DI Water and then analyzed by UV (Shimadzu UV-1200).

Figure 1:
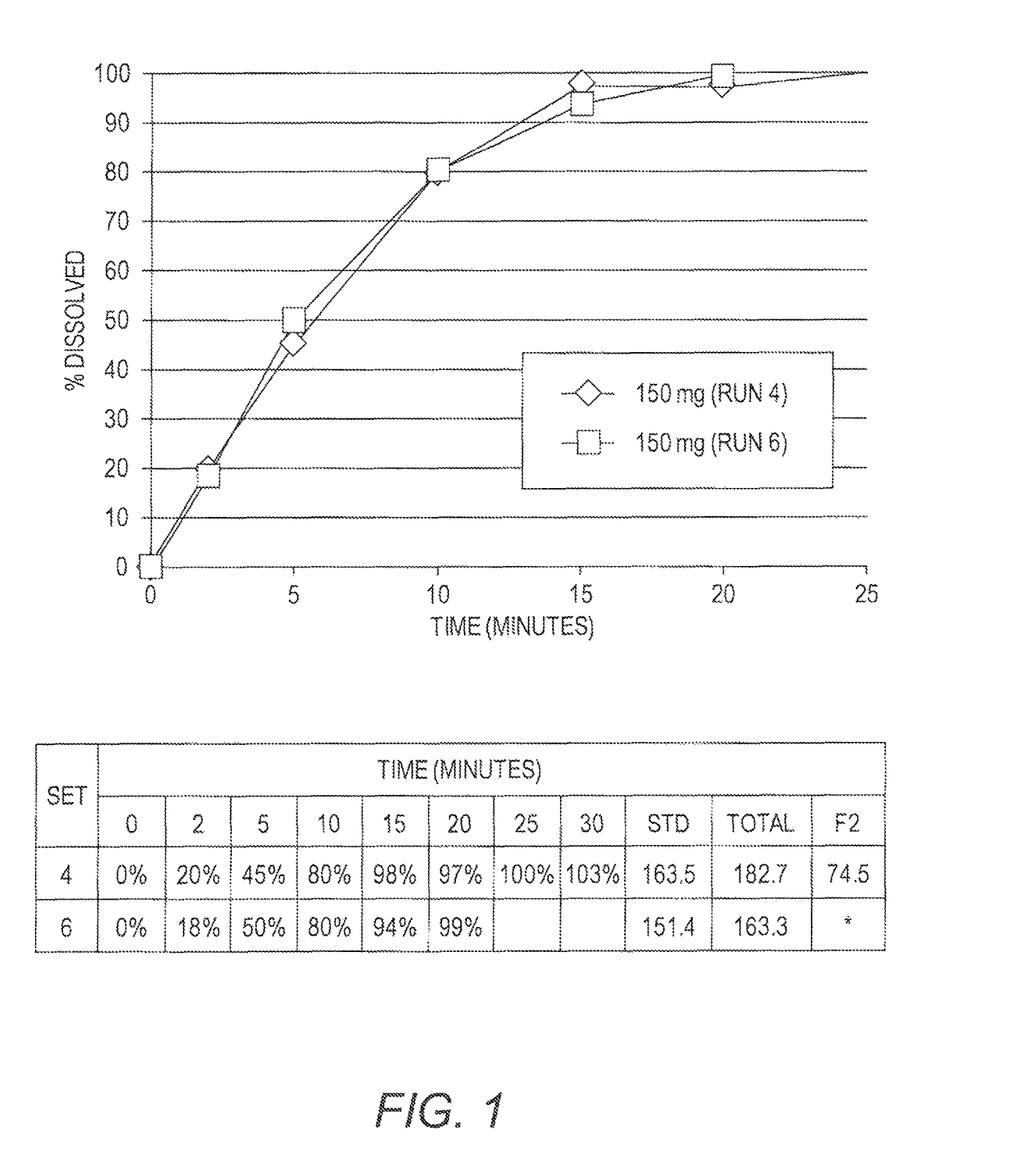
FIG. 1 shows the dissolution rate of immediate release APC tablets.

The dissolution testing was shown to be reproducible (FIG. 1). The reference 150 mg tablets (uncoated) were tested on separate days, with different media preparation of the same kind and in different sequence of media recycle.

Figure 2:
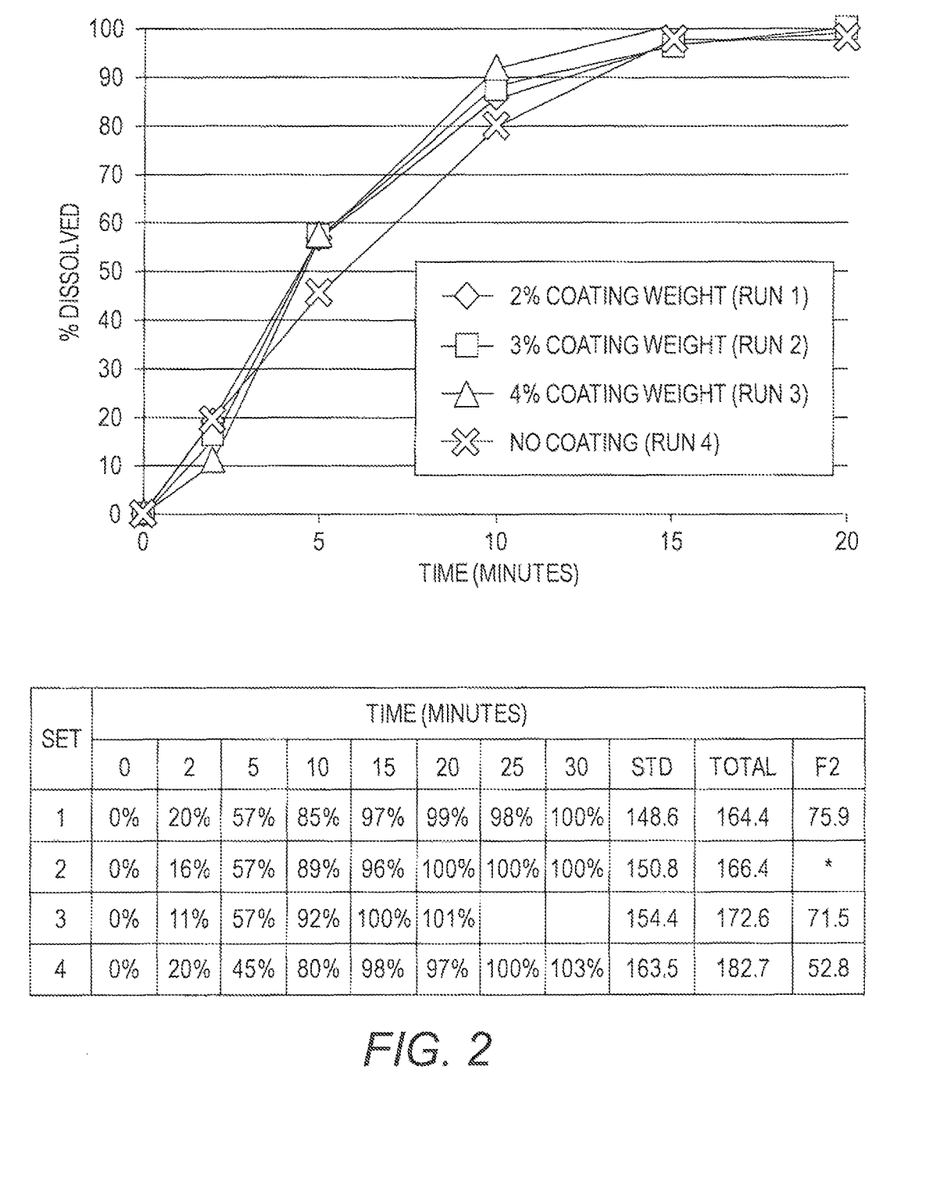
FIG. 2 shows the effect of coating on the dissolution rate of immediate release APC tablets.

The color overcoat did not meaningfully retard dissolution (FIG. 2), although a slight trend was observed at 2 minutes (higher weight caused some delay, lower dissolution). The profile appears to be faster beyond 2 minutes, relative to the reference uncoated tablets. However, this could be an effect of the process (spraying water and drying in air suspension coater) rather than the coating itself. Using the 3% target coating as a reference, all profiles are similar (F2>50) and nearly completely dissolve in 15 minutes.

Figure 3:
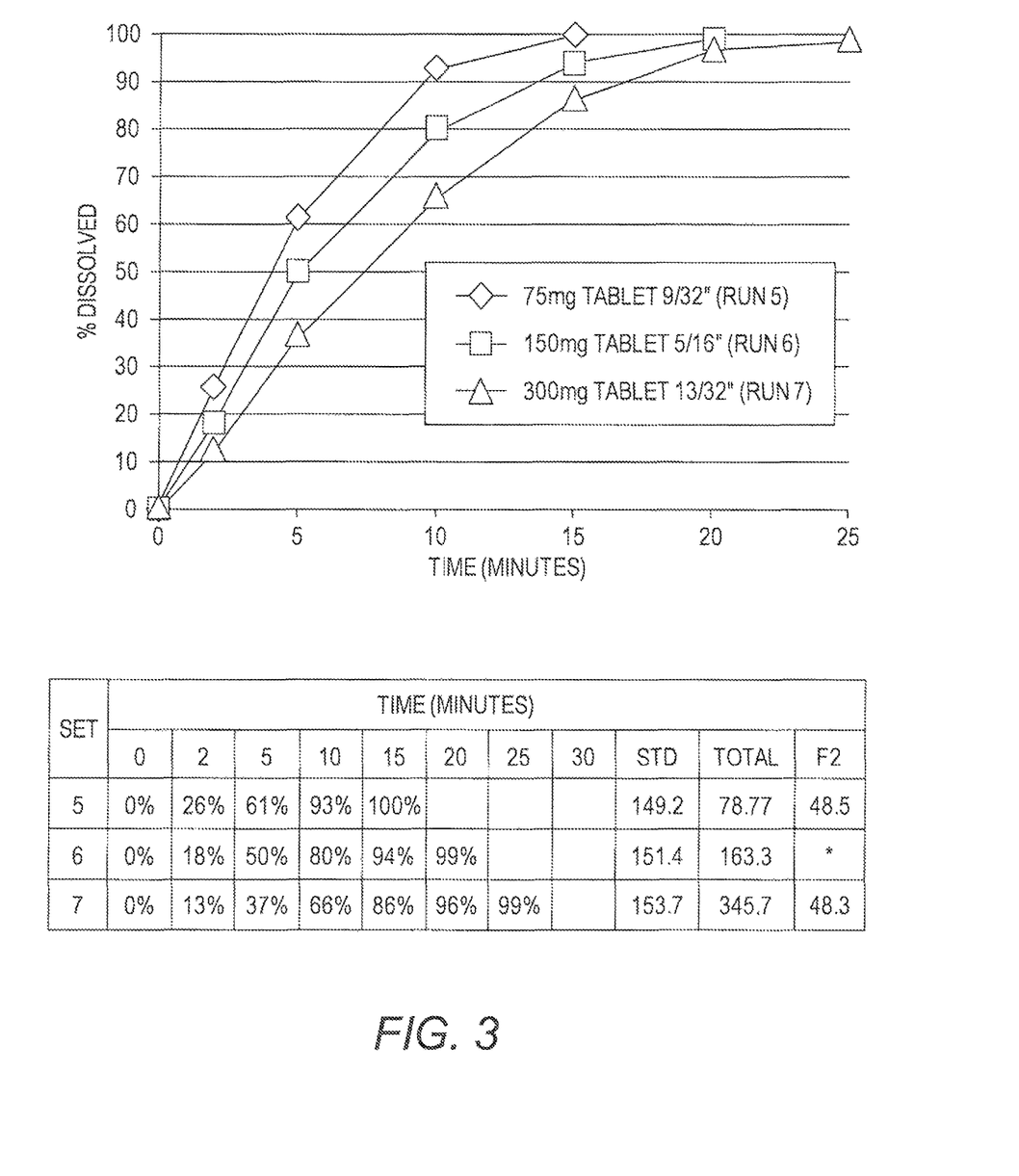
FIG. 3 shows the effect of tablet size on the dissolution rate of immediate release APC tablets.

The three doses achieved by varying tablet size of a common granulation are represented in FIG. 3. The dissolution slows as the tablet size is increased, reflecting lower values of surface area/volume as expected. All strengths dissolve>85% in 15 minutes, but the highest strength is marginal (86%). An increase in surface area/volume by using an oblong tablet resulted in a statistically significant increase in dissolution rate.

A substantial concern was the effect of media pH. Although APC will be developed as an immediate release product, FDA guidances require comparison of profiles in three media including pH 6.8 (representing intestinal pH). APC is highly soluble in water or acidic media (530 mg/ml) but its solubility is much less at pH 6.8 (26 mg/ml) (see Table 1). Remarkably, the 20-fold drop in solubility does not seem to affect the dissolution behavior, as shown in Table 2. The media used were 0.1 N HCl pH 1.2, acetate buffer pH 4.5, and phosphate buffer pH 6.8. The dissolution study was carried using 12 tablets per dose, apparatus 1 (basket), 900 ml media volume, 37° C., 100 rpm. The tablets were coated with Opadry white polymer system.

TABLE 1

Solubility of APC in 0.2M phosphate buffers

| pH of buffer | pH after equilibration | Solubility (mg/ml) |
|---|---|---|
| N/A (water) | 4.22 | 533.74 |
| 5.33 | 4.25 | 542.49 |
| 5.95 | 4.78 | 525.46 |
| 6.97 | 6.76 | 26.60 |
| 8.02 | 7.47 | 22.53 |
| 8.99 | 7.55 | 22.38 |

TABLE 2

Dissolution of APC

| | | Percent release, time (min) | | |
|---|---|---|---|---|
| Dose | Media | 5 | 10 | 15 |
| 37.5 mg | pH 1.2 | 71.9 | 99.3 | 99.7 |
| | pH 4.5 | 76.8 | 101.8 | 102.1 |
| | pH 6.8 | 69.6 | 100.2 | 100.7 |
| 75 mg | pH 1.2 | 62.9 | 98.7 | 99.4 |
| | pH 4.5 | 53.9 | 100.8 | 102.5 |
| | pH 6.8 | 57.6 | 99.4 | 100.2 |
| 150 mg | pH 1.2 | 46.8 | 96.9 | 98.4 |
| | pH 4.5 | 42.6 | 97.7 | 100.4 |
| | pH 6.8 | 42.4 | 97.4 | 100.7 |
| 300 mg | pH 1.2 | 35.0 | 91.2 | 99.5 |
| | pH 4.5 | 30.0 | 89.1 | 99.8 |
| | pH 6.8 | 31.6 | 89.9 | 100.2 |

Figure 4:
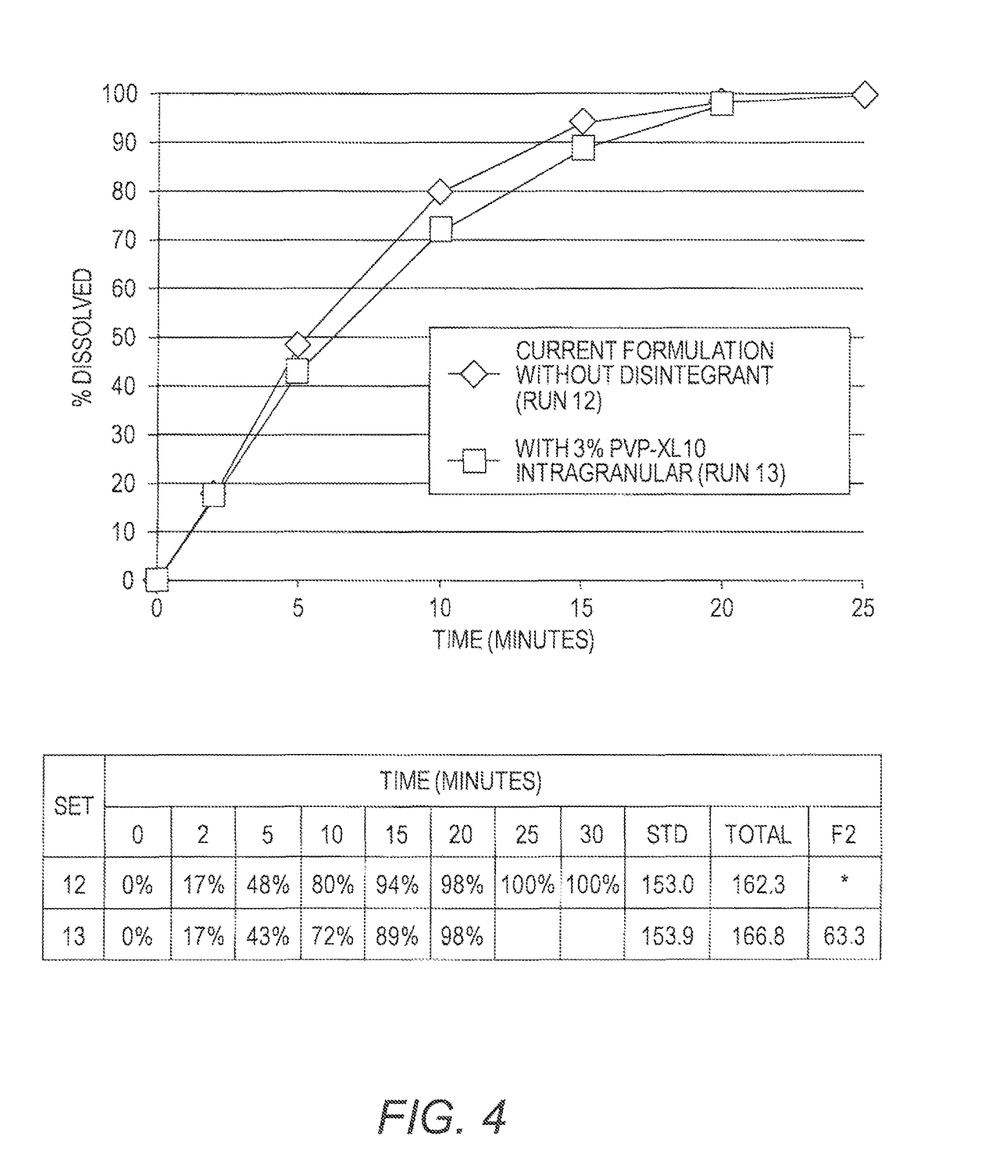
FIG. 4 shows the effect of disintegrant on the dissolution rate of immediate release APC tablets.

As mitigation of expected poorer dissolution at pH 6.8 (which was not seen as described above), one dissolution set was performed on tablets made from a formulation containing 3% superdisintegrant (PVP-XL10). The results shown in FIG. 4 confirm that a superdisintegrant will not speed release of the tablet, which dissolves rather than disintegrates. In fact, it may retard dissolution in the later stages, by the slight swelling it may cause.

Example 2

Formulation Ranges for Immediate Release Tablet

Materials included binder, drug, optional diluent, and lubricant. Binder was selected from hydroxypropyl cellulose (Klucel ExF PH, Ashland), hydroxypropyl methylcellulose (HPMC E5 premium LV, Dow), povidone (PVP K30, or Kollidon 30, BASF), and Starch 1500 (Colorcon). Lubricants were selected from magnesium stearate (Sigma Aldrich/Riedel-de-Haen), calcium stearate (Strem chemicals), and sodium stearyl fumarate (Spectrum). The optional diluent was mannitol (EMD).

Unless otherwise noted, all experiments were done in the following manner. The binder, drug, and optional diluent were admixed vigorously in a plastic container and then wet massed by hand stirring with addition of water amounting to approximately 13% of the dry mass. The wet granulation was then passed through a 16 mesh screen, dried in a 60° C. oven for no less than 1 h, and then passed through a 16 mesh screen a second time. Based on the dry granulation yield, the formula amount of lubricant was weighed and added to the cylindrical plastic container, closed, and then gently blended by hand for 24 revolutions at about a 45 degree angle. Granulation and blending involving 5 g or more material was performed in a 2×2 inch (diameter×length) cylindrical polypropylene container, and lesser quantities employed a 1×2 inch container.

The blended granulation was weighed into four 375±2 mg aliquots, each in turn added to ¹³⁄₃₂" standard round convex tooling, and compressed with application of 1 metric ton force and about 5 seconds dwell. Two tablets were each characterized for weight, hardness using a Scheuniger 6D hardness tester, and thickness using calipers. The other two tablets were dissolution tested using a USP Type 2 apparatus (paddles), 900 mL of 0.1 N HCl media at 37° C., 50 rpm, and two tablets per vessel. 0.5 mL samples of each vessel were taken at 0, 5, 10, 15, and 30 minutes. After 30 minutes, the stirring speed was increased to 150-200 rpm and maintained until the remainder of the tablets dissolved. The vessels were then sampled again for a total sample, indicating the total amount dissolved as a basis for normalizing. Each sample was then diluted with 8.50 mL DI water and scanned by UV spectrophotometer at 215 nm (Shimadzu UV-1200) using a 1.0 cm quartz flow cell. A calibration curve spanning the range of absorbance achieved was constructed based on a quadratic fit to standards, from which concentrations were derived. Dissolution results were normalized to the total concentration for each vessel at the end of dissolution testing.

To examine the effect of binder level, five individual granulations of 5 g each were made corresponding to binder levels ranging from 0 to 10% by blending binder (HPC ExF 0-0.50 g) and drug (APC 4.5-5.0 g) using the standard procedure. The dried granulations (4.8-5.0 g) were blended with 37 mg lubricant (0.75%) and compressed. The tablet properties and dissolution profile are shown in Table 3. The results show that increasing binder improves hardness but also causes a reduction in dissolution rate.

TABLE 3

Effect of binder (HPC-ExF) level from 0-10%

| Set | Gran | Binder | Mass (mg) | Thickness (mm) | Hardness (N) | Dissolution at (minutes): 5 | 10 | 15 | 30 |
|---|---|---|---|---|---|---|---|---|---|
| 1 | A1 | 0% | 374 | 4.79 | 59 | 66% | 86% | 98% | 99% |
| 2 | A2 | 1% | 374 | 4.73 | 105 | 68% | 95% | 102% | 101% |
| 3 | A3 | 2% | 373 | 4.70 | 99 | 58% | 90% | 101% | 103% |
| 4 | A4 | 5% | 375 | 4.69 | 150 | 43% | 75% | 92% | 102% |
| 5 | A5 | 10% | 375 | 4.65 | 165 | 32% | 57% | 77% | 98% |

To examine the effect of lubricant (magnesium stearate) level, a 15 g granulation was first made according to the standard procedure. This was then subdivided into 2.0 g portions, and each portion was individually blended with varying amount of magnesium stearate. The binder level was 3%. The results are shown in Table 4. The results show that lubricant had little effect on hardness as the level is increase, but caused a substantial reduction in dissolution.

TABLE 4

Effect of lubricant (magnesium stearate) level, binder fixed at 3% HPC

| Set | Gran | Lubricant | Mass (mg) | Thickness (mm) | Hardness (N) | Dissolution at (minutes): 5 | 10 | 15 | 30 |
|---|---|---|---|---|---|---|---|---|---|
| 6 | B1 | 0.00% | 374 | 4.77 | 140 | 78% | 97% | 101% | 101% |
| 7 | B2 | 0.32% | 375 | 4.76 | 130 | 71% | 93% | 101% | 99% |
| 8 | B3 | 0.52% | 374 | 4.71 | 124 | 63% | 87% | 99% | 100% |
| 9 | B4 | 0.83% | 374 | 4.72 | 126 | 57% | 83% | 96% | 100% |
| 10 | B5 | 0.99% | 375 | 4.71 | 138 | 50% | 77% | 93% | 101% |
| 11 | B6 | 1.45% | 373 | 4.67 | 125 | 41% | 69% | 85% | 99% |
| 12 | B7 | 2.51% | 373 | 4.68 | 120 | 33% | 53% | 68% | 99% |

To examine the effect of APC level, with lubricant and binder held constant, two 6-gram granulations were first prepared using 3% HPC ExF as binder. One granulation was produced without diluent, thus 97% APC, and the other had mannitol sufficient to reduce the APC loading to 86%. The two granulations were then blended in proportions to make five 2 g granulations ranging from 86% to 97% before blending. The proportions were 2.0/0 g, 0/2.0 g, 1.5/0.5 g, 1.0/1.0 g. and 0.5/1.5 g blending of the high and low granulations, respectively. Each was then blended with 15 mg magnesium stearate (0.75% level). The results are shown in Table 5. The data show that dissolution is not substantially impacted over the tested range of APC.

TABLE 5

Effect of API loading (binder HPC ExF at 3% and lubricant magnesium stearate at 0.75%)

| | | | mg | mm | N | Dissolution at (minutes): | | | |
|---|---|---|---|---|---|---|---|---|---|
| Set | Gran | API | Mass | Thickness | Hardness | 5 | 10 | 15 | 30 |
| 14 | C2 | 85.7% | 376 | 4.71 | 128 | 50% | 79% | 93% | 96% |
| 17 | C5 | 88.7% | 376 | 4.69 | 127 | 47% | 80% | 94% | 99% |
| 16 | C4 | 91.1% | 376 | 4.73 | 118 | 50% | 85% | 98% | 103% |
| 15 | C3 | 93.3% | 375 | 4.72 | 112 | 49% | 81% | 95% | 100% |
| 13 | C1 | 96.3% | 375 | 4.74 | 120 | 51% | 85% | 101% | 103% |

To examine the effect of binder type, four binders (HPMC E5, PVP K30, HPC ExF, and Starch 1500), were evaluated at two levels each (2% and 5%) by making individual 5 g granulations. The results are shown in Table 6.

TABLE 6

Effect of binder type and level (2% or 5%), magnesium stearate fixed at 0.75%

| | | | mg | mm | N | Dissolution at (minutes): | | | |
|---|---|---|---|---|---|---|---|---|---|
| Set | Gran | Binder | Mass | Thickness | Hardness | 5 | 10 | 15 | 30 |
| 18 | D1 | 2% HPMC-E5 | 375 | 4.76 | 92 | 61% | 91% | 95% | 98% |
| 19 | D2 | 2% PVP-K30 | 375 | 4.76 | 108 | 66% | 95% | 98% | 101% |
| 20 | A3 | 2% HPC-ExF | 375 | 4.69 | 128 | 56% | 87% | 97% | 99% |
| 21 | D4 | 2% Starch 1500 | 374 | 4.76 | 66 | 41% | 68% | 82% | 97% |
| 22 | D5 | 5% HPMC-E5 | 376 | 4.77 | 127 | 49% | 81% | 97% | 99% |
| 23 | D6 | 5% PVP-K30 | 377 | 4.76 | 120 | 62% | 94% | 99% | 99% |
| 4 | A4 | 5% HPC-ExF | 375 | 4.69 | 150 | 43% | 75% | 92% | 102% |
| 24 | D7 | 5% Starch 1500 | 374 | 4.76 | 66 | 29% | 51% | 64% | 90% |

To evaluate the effect of lubricant type, a single 15-gram granulation was made with 3% HPC ExF and no diluent. The dried granulation was then subdivided into 5 g aliquots. Each aliquot was then blended with one of three lubricants (magnesium stearate, calcium stearate, or sodium stearyl fumarate—"SSF") using the standard 24 turns. After the initial set of tablets was made, the remaining portion of each granulation was then vigorously shaken for 1 minute to evaluate the consequences of overblending. The standard and overblended results are shown in Table 7. Overblending had no substantial effect on tablet properties, but affected dissolution for all lubricants.

TABLE 7

Effect of lubricant type and overblending

| | | | mg | mm | N | Dissolution at (minutes): | | | |
|---|---|---|---|---|---|---|---|---|---|
| Set | Gran | Lube & blending | Mass | Thickness | Hardness | 5 | 10 | 15 | 30 |
| 25 | E1 | Mg Stearate - standard | 374 | 4.70 | 103 | 53% | 86% | 100% | 100% |
| 26 | E2 | Ca stearate - standard | 375 | 4.70 | 113 | 51% | 84% | 97% | 100% |
| 27 | E3 | SSF - standard | 374 | 4.68 | 129 | 57% | 87% | 99% | 99% |
| 28 | E1a | Mg stearate - overblend | 375 | 4.70 | 102 | 35% | 60% | 75% | 97% |
| 29 | E2a | Ca stearate - overblend | 374 | 4.68 | 91 | 40% | 69% | 86% | 100% |
| 30 | E3a | SSF - overblend | 377 | 4.70 | 138 | 44% | 72% | 89% | 98% |

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. An immediate release compressed tablet for oral delivery of (R)-2-amino-3-phenylpropyl carbamate, the tablet comprising:
   a pharmaceutically acceptable salt of (R)-2-amino-3-phenylpropyl carbamate in an amount of about 90-98% by weight of the tablet;
   at least one binder in an amount of about 1-5% by weight of the tablet; and
   at least one lubricant in an amount of about 0.1-2% by weight of the tablet;
   wherein the tablet releases at least 85% of the pharmaceutically acceptable salt of (R)-2-amino-3-phenylpropyl carbamate contained therein within a period of less than 15 minutes after administration of the tablet to a subject; and wherein the tablet exhibits substantially identical dissolution rates of the pharmaceutically acceptable salt of (R)-2-amino-3-phenylpropyl carbamate at pH 1.2, pH 4.5, and pH 6.8.

2. The immediate release compressed tablet of claim 1, wherein the tablet releases at least 95% of the pharmaceutically acceptable salt of (R)-2-amino-3-phenylpropyl carbamate contained therein within a period of less than 15 minutes after administration of the tablet to a subject.

3. The immediate release compressed tablet of claim 1, wherein the tablet does not comprise a disintegrant.

4. The immediate release compressed tablet of claim 1, wherein the at least one binder is selected from at least one of hydroxypropyl cellulose, ethylcellulose, hydroxypropyl methylcellulose, polyvinyl alcohol, hydroxyethyl cellulose, povidone, copovidone, pregelatinized starch, dextrin, gelatin, maltodextrin, starch, zein, acacia, alginic acid, carbomers (cross-linked polyacrylates), polymethacrylates, sodium carboxymethylcellulose, guar gum, hydrogenated vegetable oil (type 1), methylcellulose, magnesium aluminum silicate, and sodium alginate.

5. The immediate release compressed tablet of claim 1, wherein the at least one lubricant is selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate.

6. The immediate release compressed tablet of claim 1, comprising:
  a pharmaceutically acceptable salt of (R)-2-amino-3-phenylpropyl carbamate in an amount of about 90-98% by weight of the tablet;
  hydroxypropyl cellulose in an amount of about 1-5% by weight of the tablet; and
  magnesium stearate in an amount of about 0.1-2% by weight of the tablet.

7. The immediate release compressed tablet of claim 1, further comprising a coating.

8. The immediate release compressed tablet of claim 1, wherein the pharmaceutically acceptable salt of (R)-2-amino-3-phenylpropyl carbamate is (R)-2-amino-3-phenylpropyl carbamate hydrochloride.

9. The immediate release compressed tablet of claim 1, wherein the tablet comprises about 300 mg of the pharmaceutically acceptable salt of (R)-2-amino-3-phenylpropyl carbamate.

10. The immediate release compressed tablet of claim 1, wherein the tablet comprises about 150 mg of the pharmaceutically acceptable salt of (R)-2-amino-3-phenylpropyl carbamate.

11. The immediate release compressed tablet of claim 1, wherein the tablet comprises about 75 mg of the pharmaceutically acceptable salt of (R)-2-amino-3-phenylpropyl carbamate.

12. The immediate release compressed tablet of claim 1, wherein the tablet comprises about 37.5 mg of the pharmaceutically acceptable salt of (R)-2-amino-3-phenylpropyl carbamate.

13. The immediate release compressed tablet of claim 7, wherein the coating is a color overcoat.

14. The immediate release compressed tablet of claim 1, wherein the tablet is oblong in shape.

15. The immediate release compressed tablet of claim 1, wherein the tablet is free of other excipients.

16. The immediate release compressed tablet of claim 7, wherein the tablet is free of other excipients.

17. The immediate release compressed tablet of claim 1, comprising a pharmaceutically acceptable salt of (R)-2-amino-3-phenylpropyl carbamate in an amount of about 90-98% by weight of the tablet and a total weight of between about 30 to about 300 mg per tablet.

18. The immediate release compressed tablet of claim 1, comprising hydroxypropyl cellulose in an amount of about 1-3% by weight of the tablet.

19. The immediate release compressed tablet of claim 1, comprising magnesium stearate in an amount of about 0.1% to about 1.0% by weight of the tablet.

20. An immediate release compressed tablet for oral delivery of (R)-2-amino-3-phenylpropyl carbamate, the tablet comprising:
  a pharmaceutically acceptable salt of (R)-2-amino-3-phenylpropyl carbamate in an amount of about 90-98% by weight of the tablet and a total weight of between about 30 to about 300 mg per tablet;
  hydroxypropyl cellulose in an amount of about 1-3% by weight of the tablet; and
  magnesium stearate in an amount of about 0.1% to about 1.0% by weight of the tablet;
  wherein the tablet releases at least 85% of the pharmaceutically acceptable salt of (R)-2-amino-3-phenylpropyl carbamate contained therein within a period of less than 15 minutes after administration of the tablet to a subject; and
  wherein the tablet exhibits substantially identical dissolution rates of the pharmaceutically acceptable salt of (R)-2-amino-3-phenylpropyl carbamate at pH 1.2, pH 4.5, and pH 6.8.

21. An immediate release compressed tablet for oral delivery of (R)-2-amino-3-phenylpropyl carbamate, the tablet comprising:
  a pharmaceutically acceptable salt of (R)-2-amino-3-phenylpropyl carbamate in an amount of about 90-98% by weight of the tablet and a total weight of between about 30 to about 300 mg per tablet;
  hydroxypropyl cellulose in an amount of about 2% by weight of the tablet; and
  magnesium stearate in an amount of about 0.5% by weight of the tablet;
  wherein the tablet releases at least 85% of the pharmaceutically acceptable salt of (R)-2-amino-3-phenylpropyl carbamate or a pharmaceutically acceptable salt thereof contained therein within a period of less than 15 minutes after administration of the tablet to a subject; and
  wherein the tablet exhibits substantially identical dissolution rates of the pharmaceutically acceptable salt of (R)-2-amino-3-phenylpropyl carbamate at pH 1.2, pH 4.5, and pH 6.8.

* * * * *